United States Patent [19]
Yuen

[11] Patent Number: 6,027,728
[45] Date of Patent: *Feb. 22, 2000

[54] HERBAL SKIN REGENERATION COMPOSITION AND METHOD

[76] Inventor: Liu Yuen, 534 E. Valley Blvd., #4, San Gabriel, Calif. 91777

[*] Notice: This patent issued on a continued prosecution application filed under 37 CFR 1.53(d), and is subject to the twenty year patent term provisions of 35 U.S.C. 154(a)(2).

[21] Appl. No.: 09/129,361

[22] Filed: Aug. 5, 1998

[51] Int. Cl.$^7$ .................................................... A01N 65/00
[52] U.S. Cl. ........................... 424/195.1; 424/74; 514/783
[58] Field of Search ......................... 424/70.6, 74, 195.1, 424/450; 514/783

[56] References Cited

U.S. PATENT DOCUMENTS

| | | | |
|---|---|---|---|
| 5,055,127 | 10/1991 | Young et al. | 71/83 |
| 5,116,401 | 5/1992 | Young | 71/86 |
| 5,411,733 | 5/1995 | Hozumi et al. | 424/195.1 |
| 5,466,443 | 11/1995 | Ho et al. | 424/195.1 |
| 5,466,452 | 11/1995 | Whittle | 424/195.1 |
| 5,607,693 | 3/1997 | Bonte et al. | 424/450 |
| 5,618,537 | 4/1997 | Okpanyl | 424/195.1 |
| 5,726,180 | 3/1998 | Kurihara et al. | 514/264 |
| 5,747,538 | 5/1998 | Meybeck et al. | 514/570 |

OTHER PUBLICATIONS

"Treatment of Pediatric Exema", Nai–Jun et al, Zhejiang J. of Trad. Chin. Med, p. 262, #6, 1994.

Medline Public Access, Internet site "www.ncbi.nih.gov.", 1998.

"Intro, To Some Famous Chinese Patent Drugs", Internet site www.dmu.ac. uk/1n/cmn/current/0046.html, 1998.

*Primary Examiner*—Herbert J. Lilling

[57] ABSTRACT

The present invention comprises a selection of herbal materials with curative effects combined in a powdered form for application to human skin to accomplish skin regeneration, particularly for application to human skin affected with eczema, psoriasis, allergic reactions, inflammatory rash and the like. The process of application is critical to effectiveness of the present invention. The application of the herbal powder to the skin is intended to cause a temporary inflammation which removes at least an upper skin layer, with some mild to noticeable discomfort, and causes accelerated skin regeneration so that soft, unaffected skin replaces the scaling and/or lesioned skin.

3 Claims, No Drawings

HERBAL SKIN REGENERATION COMPOSITION AND METHOD

BACKGROUND OF THE INVENTION

The present invention relates to herbal skin regeneration compositions and methods of application to human skin to accomplish such skin regeneration, particularly for application to human skin affected with eczema, psoriasis, allergic reactions, inflammatory rash and the like.

Chinese medical arts rely heavily on compositions prepared and specially administered from among a relatively large selection of raw and processed herbal materials. The following are examples of such materials and applications related to human health, especially related to skin and connective tissue health.

The Panax family is known by its numerous varieties, the best known of which are as follows: *Panax ginseng* (C. A. Meyer), which is most frequently used for its medical attributes, *Panax notoginseng, Panax pseudo-ginseng* (subsp. *himalaicus*), *Panax japonicus* (var. major; var. *angustifolius*), *Panax quinquefolium, Panax trifolius, Panax zingiberensis* and *Panax stipuleanatus*. *Panax ginseng* seems to be among the most saponin-rich and the most effective. Panax originate essentially from Japan, China and Korea. The varieties cultivated in these different zones can be slightly different and are exposed to different geoclimatic conditions. Very different saponin contents are found in the different parts of the plant. The root part is the most frequently used and generally the most active. The highest saponin content is observed in the end of the root (ninjin in Japanese) and in the hairy roots (keninjin in Japanese). Planta Med. 1990, 56(1), 19–23, describes its use as an anti-inflammatory. As described in U.S. Pat. No. 5,747,538, ginsenoside R0 and plant extracts in which it is present have a stimulating activity on the synthesis of collagen, particularly collagens of types I and III, hereafter abbreviated respectively to "collagen I" and "collagen III".

Now, type I collagen represents 80 to 90% of the total skin collagen, the remainder, i.e. about 10 to 15% of the total skin collagen, consisting mainly of type III collagen. Type I and type III collagens are very intimately associated to form fibers within the dermis (BOREL J. P., MONBOISSE J. C., C. R. Soc. Biol. (1993), 187, 124–142; LAPERE C. M., Br. J. Dermatol. (1990), 122, 5–11).

Thus, irrespective of its origin, whether it be spontaneous as in the case of natural aging, or whether it be induced by a pathological condition, by drugs or by exposure to ultraviolet radiation, the decrease in the proportion of collagens I and III can be slowed down, or even stopped, by carrying out the process of U.S. Pat. No. 5,747,538 in order to stimulate collagen synthesis.

In addition, the article, "Research and development of cancer chemopreventive agents in China". J Cell Biochem Suppl. 1997; 27: 7–11, indicates that red ginseng, a processed *Panax ginseng*, is considered a typical tonic in traditional Chinese medicine. The studies demonstrated that red ginseng extract inhibited DMBA-induced skin papilloma significantly.

The genus Prunus (wild plum) has been reported to have skin-affective properties. In Biol Pharm Bull 1994 October 17(10):1417–1420, "Studies of cuticle drugs from natural sources. II. Inhibitory effects of Prunus plants on melanin biosynthesis", Matsuda H, Nakamura S, Kubo M, it was reported that the leaves of *P. zippeliana* inhibit melanin biosynthesis which is involved in hyperpigmentation and could be used as a whitening agent for the skin.

Some herbal preparations result in temporary skin inflammation. In Cutis 1993 June; 51(6):424, "Honeysuckle contact dermatitis", Webster R M, there is a case report and discussion of linear itchy raised blisters on the wrist of a patient that pulled Hall's Japanese honeysuckle (*Lonicera japonica holliana*). Also reported are results of antimicrobial action of flos Lonicera.

In Yakugaku Zasshi 1989 February; 109(2):113–118, "Studies on chemical protectors against radiation. XXVI. Protective effect of various extracts on crude drugs on skin injury induced by X-irradiation", Sato Y, Ohta S, Sakurai N, Shinoda M, the protective potency against skin injury on mice induced by X-irradiation was studied by use of 72 extracts of crude drugs. The protective potency was determined according to the degrees on skin injury after irradiation of 1100R, 30 k Vp soft X-ray. As a result of these study, 16 kinds of crude drugs such as *Rosae Fructus, Aloe arborescens* (*Herba*), *Citri Leiocarpae Exocarpium, Schizonepetae Spica, Evodiae Fructus, Bupleuri Radix, Corni Fructus, Perillae Herba, Anemarrhenae Rhizoma, Menthae Herba, Trapae Fructus, Angelicae Dahuricae Radix, Sinomeni Caulis et Rhizoma, Ephedrae Herba, Acer nikoense* (*Cortex*), *Forsythiae Fructus*, revealed protective potencies on skin injury.

*Herba Taraxaci*, common name dandelion, has been shown in use as a poultice of pulverized leaves mixed with dough applied to a bad bruise. Robbins W. W., J. P. Harrington and B. Freire-Marreco, 1916, "Ethnobotany of the Tewa Indians", Publication SI-BAE Bulletin #55, p. 61.

In the article, "Thermal and antiradical properties of indirect moxibustion", Am J Chin Med 1997; 25(3–4): 281–287, Chiba A, Nakanishi H, Chichibu S, the thermal and antiradical properties of indirect moxibustion stimulation were investigated by thermal qualitative and spectroscopic methods. The thermal effect of indirect moxibustion was mainly dependent on the spacing distance between the moxa and skin, and not on the moxa weight. The radical scavenging activities of moxa and moxa-tar were measured by a photometric absorbance method, chemical reaction with 1,1-diphenyl-2-picrylhydrazyl. The obtained results indicate that the inhibitory effects of moxa and moxa-tar on superoxide production are due to the radical scavenging mechanism.

In the article, "Main pharmacological roles and clinical curative effect of sanbi rebao", Chung Hsi I Chieh Ho Tsa Chih, 1990 September; 10(9):545–546, Zhao D K, Xu H Q, Liu J S, Sanbi Rebao (contain 32 components, such as *Radix Aconiti, Rhizoma Chuanxiong, Semen Strychni, Radix Glycyrrhizae, Radix Angelicae sinensis, Radix Ledebouriellae, Fructus Evodiae, borneolum syntheticum*, etc.) had antagonistic action on the ear swollen response induced by croton oil and on the ear inflammation reaction caused by dimethylphenylene in mice. It could decrease significantly the response rate of turning its body induced by acetic acid, increase the pain threshold caused by warm, reduce the surface seepage of injure skin and accelerate the wound recovery. The above results showed Sanbi Rebao possessed the roles of dephlogisticate, analgesia and promoting wound recovery, Besides these, clinic research indicated that effective rate of Sanbi Rebao on pain or numbness caused by cold, damp and wind (rheumatism) was 97%.

In the article "Clinical and experimental study of burns treated locally with Chinese herbs", Chung Hsi I Chieh Ho Tsa Chih 1991 December; 11(12):727–729, Wang G D, Zhang Y M, Xiong X Y, the authors decsribe selecting some traditional herbs to cure a burn wound, which had not only the function of improving the local microcirculation of the burned surface and their bactericidal action, but also the function of changing the bacterial growth milieu action. *Coptis chinensis* 40%, *Herba Taraxaci* 40%, *Fructus Mume* 10% and *Salvia miltiorrhizae* 10% were boiled, infiltrated and disinfected. The mixture thus made was called as Burn II, which were applied on the burned surface daily, 97.1% of 103 patients were cured. Through the experiment of 60 rabbits burned by irons, which were divided into 6 groups (n=10 in each group) and each 2 groups infected respectively with *Bacillus pyocyaneus, Bacillus Coli* and *Staphylococcus Aureus*, took one of each infected group as control group. After 14 days, the infected burned surfaces which were applied with Burn II daily. The results showed that the effect of Burn II was not only significant, but also its usage was not highly restricted by the medical condition.

In the article "Inhibition of Na+,K(+)-ATPase by 1,2,3,4,6-penta-O-galloyl-beta-D-glucose, a major constituent of both *moutan cortex* and *Paeoniae radix*", Biochem Pharmacol 1997 February 21; 53(4):611–614, Satoh K, Nagai F, Ushiyama K, Yasuda I, Seto T, Kano I, the inhibition of Na+,K(+)-ATPase activity by various constituents of Moutan Cortex and *Paeoniae Radix* was studied. 1,2,3,4,6-Penta-O-galloyl-beta-D-glucose (PGG), a major component of both crude drugs, strongly inhibited Na+,K(+)-ATPase activity (IC50=2.5×10(−6) M), whereas galloylpaeoniflorin, benzoic acid, and catechin were weakly inhibitory, and albiflorin, oxypaeoniflorin, paeoniflorin, paconol, and phenol were ineffective. The inhibition of Na+,K(+)-ATPase activity by PGG was decreased in the presence of BSA or phospholipids. The inhibition mode of PGG was noncompetitive with respect to ATP. The K0.5 value for Na+ was increased by the addition of PGG from 9.1 to 12.3 mM, whereas that for K+ was not altered. PGG also inhibited K(+)-dependent p-nitrophenyl phosphatase activity with an IC50 value of 5.3×10(−6) M, and the extent of the inhibition increased at higher concentrations of K+. The K0.5 value for K+ was decreased by the addition of PGG from 3.3 to 2.0 mM. These results suggested that the inhibition of Na+,K(+)-ATPase activity is caused by interaction of PGG with the enzyme in the E2 state. The inhibitory effect of *Moutan Cortex* or *Paeoniae Radix* is considered to be mainly attributable to PGG.

In the article, "Research on hemostatic constituents in carbonized *Schizonepeta tenuifolia* Brig", Chung Kuo Chung Yao Tsa Chih 1993 September; 18(9):535–538, Ding N W, Kong L D, Wu H, Wang S L, Long Q J, Yao Z, Chen J, it has been shown that the fat soluble extract SeE from carbonized *Schizonepeta tenuifolia* has an obvious hemostatic action. In a given range of dose there is a significant linear correlation between the logarithms of its doses and the reciprocal of the bleeding and coagulating times in mice. Obvious hemostatic action was observed after mice had been administered in ip and po respectively for 0.5 h and 1 h. The hemostatic time of the former was 6 h and the latter 12 h. The LD50 of StE in po was 2.652+/−0.286 g/kg, while in ip 1.945 4/−0.207 g/kg.

In the article "Effect of the basidiomycete *Poria cocos* on experimental dermatitis and other inflammatory conditions", Chem Pharm Bull (Tokyo) 1997 March; 45(3):492–494, Cuellar M J, Giner R M, Recio M C, Just M J, Manez S, Rios J L, the hydroalcoholic extract from *P. cocos* was examined for oral and topical anti-inflammatory activities. It proved to be active against carrageenan, arachidonic acid, tetradecanoyl phorbol acetate (TPA) acute edemas, TPA chronic inflammation and oxazolone delayed hypersensitivity in mice. Two lanostane-type triterpenes were isolated and identified by spectroscopic methods as dehydrotumulosic and pachymic acids. Their ID50 on acute TPA edema was 4.7×10(−3) and 6.8×10(−4) mumol/ear, respectively.

The above are reprintings of abstracts available at the InterNet Web site of the National Center for Biotechnology Information with an address at "www.ncbi.nlm.nih.gov./htbin-post/query?" for access to MEDLINE's abbreviated database available to the public.

At the InterNet Web site with an address at "www.dmu.ac.uk/ln/cmn/current/0046.html", the following was reported "6. INTRODUCTION OF SOME FAMOUS CHINESE PATENT DRUGS (SERIES 6), ZhiKe PiPa TangJiang (Cough Syrup of Loquat Leaf), PRINCIPAL INGREDIENTS: Loquat leaf (*Folium Eriobotryae*), Platycodon root (*Radix Platydoci*), Stemona root (*Radix Stemonae*), Cogongrass rhizome (*Rhizoma Imperatae*), ACTIONS: Resolving phlegm and relieving cough. INDICATIONS: Dysfunction of the lung-qi, manifested as cough, difficult expectoration in abundance. It is often used clinically for the treatment of cough dueto common cold. ADMINISTRATION AND DOSAGE: To be taken orally, 5–10 ml each time, 3 times a day, half of the amount for children. PACKING: Syrup, 100 ml per bottle. MANUFACTURER: Fuzhou Traditional Chinese Pharmaceutical Factory 324 Xiateng Road, Fuzhou, FuJian Province, P.R. China".

The publication "The Treatment of Pediatric Eczema with Shu Feng Qu Shi Tang" by Zhan Nai-jun, Zhe Jiang Zhong Yi Za Zhi (Zhejiang Journal of Traditional Chinese Medicine), #6, 1994, p. 262, describes the action, in combination with several other herbal components, of *Fructus Kochiae Scopariae* (Di Fu Zi), as effective in the healing of a eczematic lesion after itching had been eliminated by another composition without that component.

SUMMARY OF THE INVENTION

The present invention comprises a selection of herbal materials with curative effects combined in a powdered form for application to human skin to accomplish skin regeneration, particularly for application to human skin affected with eczema, psoriasis, allergic reactions, inflammatory rash, skin ulceration scarring, several tineas (*tinea corporis, tinea unguium, tinea capitis, tinea pedis, tinea manuum, tinea cruris, tinea barbae, tinea versicolor, tinea oral, cutaneous candidosis*). Swollen, numb and sore extremities (hand and foot) have responded well with reduced symptoms with treatments according to the present invention.

The process of application is critical to effectiveness of the present invention. The application of the liquid extract of the herbal powder to the skin is intended to cause a temporary inflammation which removes at least an upper skin layer, with some mild to noticeable discomfort, and causes accelerated skin regeneration so that soft, unaffected skin replaces the scaling and/or lesioned skin.

The process of application requires that the powdered herbal materials are immersed in a mixture of boiling water and rice vinegar (about 3% acetic acid). The resulting liquid extract (which includes, as the term is used herein, substantial amounts of undissolved, albeit softened, vegetable matter), when cooled, is bathed or rubbed on the affected skin surface, preferably with a soft towel. This method of liquid extract preparation and application is preferably repeated 1–3 times per day. As used herein, a treatment course will comprise use of 5 separate acts of liquid extract preparation and application thereof. A mild case of skin problems is treated with 1–3 treatment courses. The most serious and stubborn of skin problems will require up to 20 treatment courses.

Individually, the components of the skin regeneration powder have medicinal value and/or are reactive with human skin chemistries. The combination of these components has not been previously thought to produce a substantially complete and accelerated skin removal and regeneration with the treatment method described below.

It is apparent that the accelerated skin removal is somewhat related to inducing a chemical pseudo-"burn" on a patient's skin. The prior art does not indicate that the skin regeneration powder of the present invention would result in an initial pseudo-"burn" of the affected skin with just sufficient removal of the skin to avoid a permanent scar and thereafter to promote accelerated new skin generation from the lower dermal layers. The discomfort to the patient has been found to be at an acceptable level in view of the substantial healing benefits of the present invention. Long term healing without return of the prior skin condition has occurred in a number of treated patients.

DETAILED DESCRIPTION OF THE INVENTION

The following is a list of skin regeneration powder components and approximate weight percents for each component in the that skin regeneration powder:

| Component Name | Weight Percent |
| --- | --- |
| Prunus Mume Sieb | 2.0 |
| Cortex Dictamniradisis | 2.0 |
| Herba Menthae | 5.0 |
| Encedanium Regidum | 2.0 |
| flos Lonicerae | 8.0 |
| Radix Angelicae Pubescentis | 2.0 |
| Herba Taraxaci | 4.0 |
| Radix Stemonae | 3.0 |
| Alum | 8.0 |
| Herba Schizonepetae | 6.0 |
| Cortex Poria | 3.0 |
| Korean Red Ginseng | 3.0 |
| Di Fu Zi | 5.0 |
| Wu Zu Yu | 6.0 |
| Tribulus Terrestris | 3.0 |
| Fructus Cnidii | 5.0 |
| Radix Ledebouriellae | 5.0 |
| Radix Clematidis | 5.0 |
| Herba Moxa | 3.0 |
| Periostracum Cicadae | 5.0 |
| Radix Paenoniae Rubra | 3.0 |
| Sophora Flavescens Aiton | 6.0 |
| Asarum Chinese Wild Ginger | 6.0 |
| | 100.0 |

It will be appreciated to those skilled in this art that the above approximate weight percents are dependent on generally expected potencies of the components, whereby the relative weight percents will vary sometimes substantially from the above individual amounts. It will be within the skilled person's knowledge with this disclosure that the objects of the present invention require the inclusion of each of the components in relative approximate weight percents above. As disclosed in the prior art, individual components comprise medicinal effects on the epidermis and dermis and are further comprise substantially absorbable molecular classes. Subgroups within the above list comprise those components which have similar known effects, i.e., some components have been shown to have substantial skin regeneration effects while others comprise skin irritant and/or astringent effects.

The above components are ground to a powder form well known in the Chinese herbal art. Such grinding may be accomplished manually with the components separately ground or ground together. The powder mixture is preferably substantially finer than 100 mesh. Each of the components in the above ranges is required to obtain the objects of the present invention.

A solution of a single liquid extract contains approximately 112 grams (dry weight) of the ground powder. The dry powder is placed in a boiling liquid of about 7.5 liters of water and one liter of rice vinegar and allowed to extract components of the powdered components by continued immersion throughout the subsequent cooling and application process. The length of time for extraction will necessarily depend on a desired strength of the extract liquid, although an extraction time of at least 5 minutes is required. The resulting extract liquid will have taken on a light brown color. The density and viscosity of the extracted liquid will be about the same as that of water.

This extract liquid is slightly acidic and comprises a highly complex mixture medicinally active molecules from the powdered components. The extract liquid must be used immediately upon cooling to a temperature just acceptable to the patient. It is believed from the relative lack of effectiveness of the extract liquid after about two hours that a continuing set of reactions occurs among the medicinally effective extracted molecules.

For the application steps, it is preferred that the extract liquid is retained in contact and in the same container in which the boiling extraction takes place. The extract liquid is absorbed into a towel or similar liquid absorbing material and applied to the affected skin area by rubbing at least about 20 minutes and more preferably about 30 minutes, refreshing the extract liquid in the liquid absorbing material about every minute. The application to the affected skin must be relatively softly, preferably by hand and with some gentle soaking of the affected area, although the degree of physical abrasion with the application cloth is determined primarily by the amount of callous in the affected area, i.e., the palm of the hand and soles of the feet will be rubbed at least gently and the face is only bathed without rubbing. The affected area must be washed with water after each application is complete. The treated area is then preferably dried and optionally covered with a tinea plaster and/or antiphlogistine. A light protective bandaging or covering is preferred between applications at the affected area, as emerging skin layers may be exposed to infection, as burn patients often are substantially exposed to substantial air-borne infection risk as new tissue develops in the burned area.

The patient will experience a mild to substantial burning sensation on application of the extract liquid, perhaps extending to a mild pain at the application area. Practice indicates that the discomfort is bearable for the patient with careful attention to the amount and strength of extract liquid applied to the affected skin area. After a single treatment course of five sets of extract liquid preparation and application at the rate of 1–3 sets of such extract liquid preparation and application per day, the patient must wait at least 34 days. The affected skin area in that 3–4 day period will become substantially reddened beneath an overlay of scaling and flaking skin.

Where the skin problems have persisted for 3–5 years, experience indicates that 3–5 treatment courses will be required to substantially eliminate the problem skin from re-emerging. Where the skin problems have persisted for 10–20 years, experience indicates that up to 20 treatment courses will be required to substantially eliminate the problem skin from re-emerging.

The extract liquid is absorbed into the skin and to some extent into the connective tissue beneath it. It is highly recommended that the patient reduce or eliminate absorbable skin contact with alkali fluids or such foods and drink that promote a relatively basic blood chemistry. Some foods that the patient should avoid are shellfish, beef and fruits such as mango.

The extract liquid should never be taken internally or around the eyes. The extract liquid is to be used with extreme care, preferably not at all, by those with very sensitive skin, lupus erythematosus, scarlet fever or other such skin affective diseases, wounds or pregnant women. Because some skin bleaching is accomplished with the extract liquid, those with darker skin pigments should not use the extract liquid unless with the acceptance that affected area after treatment with the method of the present invention will be regenerated with substantially lighter skin.

The above composition and methods present the skilled person with considerable and wide ranges from which to choose appropriate obvious modifications for the above examples. However, the objects of the present invention will still be obtained by the skilled person applying such disclosures in an appropriate manner.

I claim:

1. A skin regeneration powder comprising, according to the following list by approximate weight percents:

*Prunus Mume Sieb* at about 2.0%;
   *Cortex Dictamniradisis* at about 2.0%;
   *Herba Menthae* at about 5.0%;
   *Encedanium Regidum* at about 2.0%;
   *flos Lonicerae* at about 8.0%;
   *Radix Angelicae Pubescentis* at about 2.0%;
   *Herba Taraxaci* at about 4.0%;
   *Radix Stemonae* at about 3.0%;
   Alum at about 8.0%;
   *Herba Schizonepetae* at about 6.0%;
   *Cortex Poria* at about 3.0%;
   Korean Red Ginseng at about 3.0%;
   Di Fu Zi at about 5.0%;
   Wu Zu Yu at about 6.0%;
   *Tribulus Terrestris* at about 3.0%;
   *Fructus Cnidii* at about 5.0%;
   *Radix Ledebouriellae* at about 5.0%;
   *Radix Clematidis* at about 5.0%;
   *Herba Moxa* at about 3.0%;
   *Periostracum Cicadae* at about 5.0%;
   *Radix Paenoniae Rubra* at about 3.0%;
   *Sophora Flavescens Aiton* at about 6.0%; and
   Asarum Chinese Wild Ginger at about 6.0%.

2. An aqueous, slightly acidic liquid extract from a skin regeneration powder, the powder comprising according to the following list by approximate weight percents:

*Prunus Mume Sieb* at about 2.0%;
   *Cortex Dictamniradisis* at about 2.0%;
   *Herba Menthae* at about 5.0%;
   *Encedanium Regidum* at about 2.0%;
   *flos Lonicerae* at about 8.0%;
   *Radix Angelicae Pubescentis* at about 2.0%;
   *Herba Taraxaci* at about 4.0%;
   *Radix Stemonae* at about 3.0%;
   Alum at about 8.0%;
   *Herba Schizonepetae* at about 6.0%;
   *Cortex Poria* at about 3.0%;
   Korean Red Ginseng at about 3.0%;
   Di Fu Zi at about 5.0%;
   Wu Zu Yu at about 6.0%;
   *Tribulus Terrestris* at about 3.0%;
   *Fructus Cnidii* at about 5.0%;
   *Radix Ledebouriellae* at about 5.0%;
   *Radix Clematidis* at about 5.0%;
   *Herba Moxa* at about 3.0%;
   *Periostracum Cicadae* at about 5.0%;
   *Radix Paenoniae Rubra* at about 3.0%;
   *Sophora Flavescens Aiton* at about 6.0%; and
   Asarum Chinese Wild Ginger at about 6.0%.

3. A method for skin regeneration comprising:

(a) preparing a liquid extract from a skin regeneration powder comprising, according to the following list by weight percents:
   *Prunus Mume Sieb* at about 2.0%;
   *Cortex Dictamniradisis* at about 2.0%;
   *Herba Menthae* at about 5.0%;
   *Encedanium Regidum* at about 2.0%;
   *flos Lonicerae* at about 8.0%;
   *Radix Angelicae Pubescentis* at about 2.0%;
   *Herba Taraxaci* at about 4.0%;
   *Radix Stemonae* at about 3.0%;
   Alum at about 8.0%;
   *Herba Schizonepetae* at about 6.0%;
   *Cortex Poria* at about 3.0%;
   Korean Red Ginseng at about 3.0%;
   Di Fu Zi at about 5.0%;
   Wu Zu Yu at about 6.0%;
   *Tribulus Terrestris* at about 3.0%;
   *Fructus Cnidii* at about 5.0%;
   *Radix Ledebouriellae* at about 5.0%;
   *Radix Clematidis* at about 5.0%;
   *Herba Moxa* at about 3.0%;
   *Periostracum Cicadae* at about 5.0%;
   *Radix Paenoniae Rubra* at about 3.0%;
   *Sophora Flavescens Aiton* at about 6.0%; and
   Asarum Chinese Wild Ginger at about 6.0%;

(b) applying the liquid extract to a skin surface for about more than 20 minutes;

(c) repeating steps (a) and (b) at least four times; and (d) withholding exposure of the skin surface to the extract liquid for about at least three days.

* * * * *